United States Patent [19]
Wilkoff

[11] Patent Number: 4,990,155
[45] Date of Patent: Feb. 5, 1991

[54] SURGICAL STENT METHOD AND APPARATUS

[76] Inventor: Howard M. Wilkoff, 88 Hickory Rd., Weston, Mass. 02193

[21] Appl. No.: 354,185

[22] Filed: May 19, 1989

[51] Int. Cl.$^5$ .............................................. A61M 29/00
[52] U.S. Cl. .................................... 606/191; 606/194; 606/198
[58] Field of Search ................ 606/191, 194, 198, 200

[56] References Cited

U.S. PATENT DOCUMENTS

| | | | |
|---|---|---|---|
| 3,993,057 | 11/1976 | Ramwell | 128/833 |
| 4,503,569 | 3/1985 | Dotter | 606/200 X |
| 4,553,545 | 11/1985 | Maass et al. | 606/198 |
| 4,649,922 | 3/1987 | Wiktor | 606/194 |
| 4,655,771 | 4/1987 | Wallsten | 606/198 X |
| 4,781,683 | 11/1988 | Woznlak et al. | 604/110 |

Primary Examiner—Robert A. Hafer
Assistant Examiner—Kerry Owens
Attorney, Agent, or Firm—John E. Toupal; Harold G. Jarcho

[57] ABSTRACT

A method for preventing arterial restenosis after angioplasty and including the steps of providing from a plastic material filament a base coil of a substantially uniform given diameter, inducing in the base coil an elastic memory that provides an inherent tendency thereof to return to the given diameter after any distortion, forming from the base coil a coil stent with a substantially uniform predetermined diameter substantially less than the given diameter, releasably coupling the coil stent to an elongated delivery device adapted to pass through a blood carrying vessel, inserting the coil stent and delivery device into a vessel, and manipulating the delivery device within the vessel so as to position the coil stent at a desired location therein. After placement, the coil stent is decoupled from the delivery device which is removed from the vessel, and the elastic memory is allowed to expand the coil stent into contact with the inner walls of the vessel and to the diameter substantially greater than the predetermined diameter. The use of an inherently expandable plastic coil stent permits the effective prevention of restenosis in small arteries typically found in the area of the heart.

21 Claims, 1 Drawing Sheet

U.S. Patent
Feb. 5, 1991
4,990,155
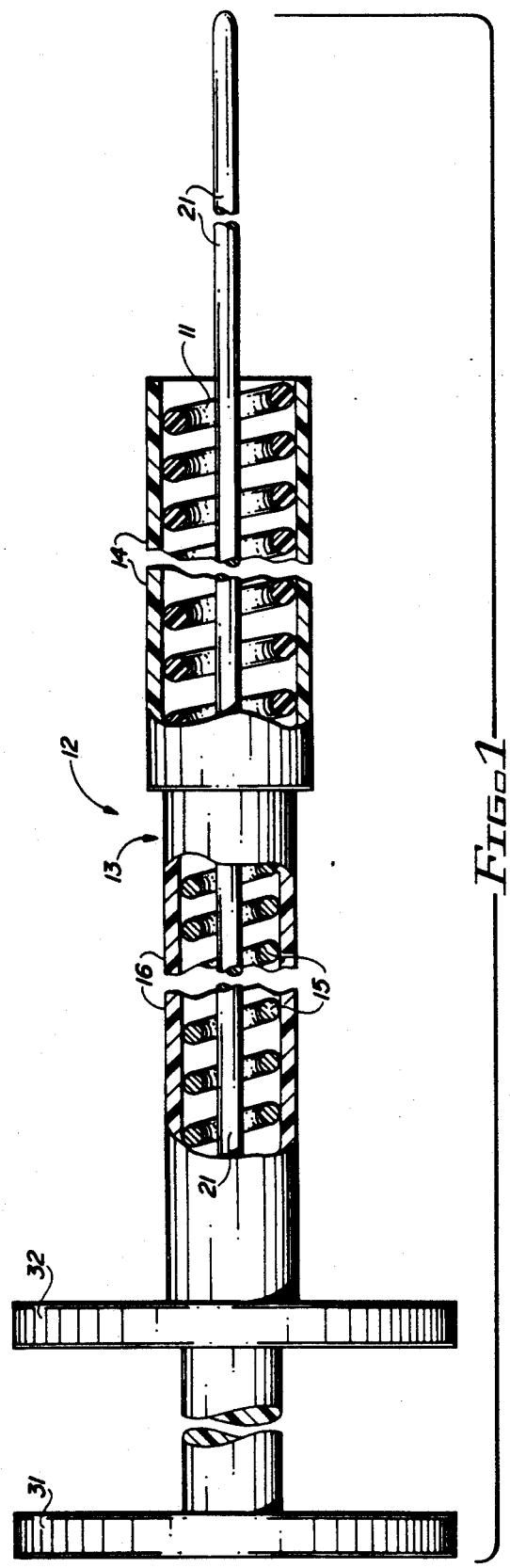
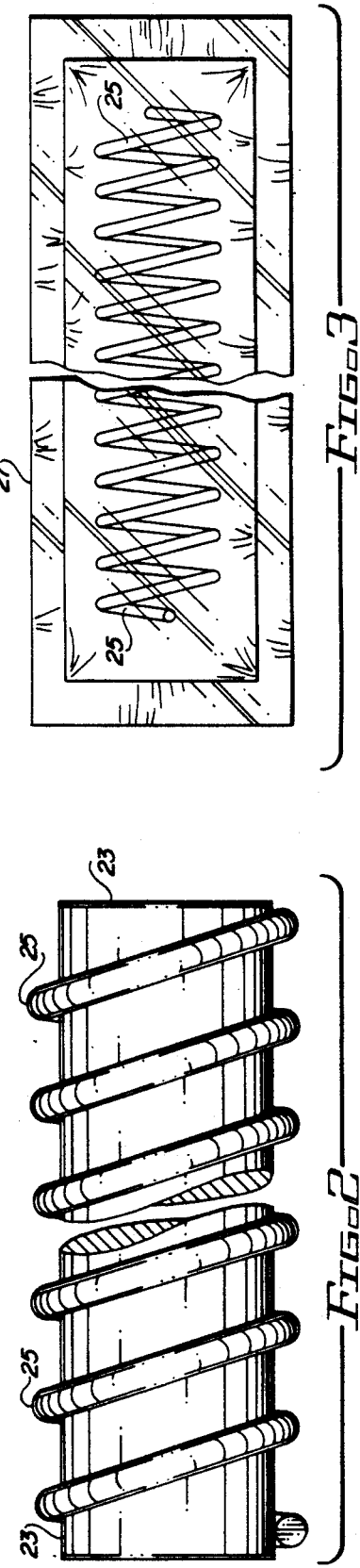

SURGICAL STENT METHOD AND APPARATUS

SUMMARY OF THE INVENTION

This invention relates generally to a method and apparatus for the prevention of arterial restenosis and, more particularly, to such a method employing an inherently expandable plastic stent.

Percutaneous transluminal balloon angioplasty is used commonly for opening of stenoses of the peripheral and coronary arteries. During this procedure, an uninflated balloon is delivered by a catheter into a narrowed portion of an arterial lumen. The balloon then is inflated to outwardly expand the stenotic plaque thereby enlarging the luminal diameter and improving distal perfusion. After deflation, the balloon and catheter are withdrawn from the body. Typically, a significant improvement in blood flow occurs initially after angioplasty. However, within a period of several months, a significant percentage of treated arteries experience restenosis and again seriously reduced blood flow.

Various types of intravascular stents have been developed in attempts to prevent restenosis and thereby retain patentcy of a treated artery so as to retain an adequate blood flow. For example, U.S. Pat. Nos. 3,868,956 and 4,512,338 disclose the use of intravascular stents formed of a shape memory alloy such as nitinol. After implantation electrical energy is applied to the alloy formed stent causing radial expansion thereof within a receptor vessel. Other types of expandable intravascular stents are disclosed in U.S. Pat. Nos. 4,553,545 and 4,768,507. Each of these patents discloses a method for percutaneous transluminal insertion of a coiled metal spring stent that is mechanically restrained under tension in a contracted state during delivery to a predetermined position within a vessel of a living body. After placement, the mechanical restraint is released allowing the coil spring stent to expand radially against the inner walls of the encompassing vessel. All of these prior expandable coil stents have exhibited significant disadvantages. For example, activation of memory alloy stents requires the application of heat which can produce undesirable tissue damage or blood coagulation while metal spring stents require catheter delivery systems that are inherently functionally limited.

The object of this invention, therefore, is to provide an improved intravascular stent and method for the prevention of arterial restenosis.

SUMMARY OF THE INVENTION

The invention is a method for preventing arterial restenosis after angioplasty and including the steps of providing from a plastic material filament a base coil of a substantially uniform given diameter, inducing in the base coil an elastic memory that provides an inherent tendency thereof to return to the given diameter after any distortion, forming from the base coil a coil stent with a substantially uniform predetermined diameter substantially less than the given diameter, releasably coupling the coil stent to an elongated delivery device adapted to pass through a blood carrying vessel, inserting the coil stent and delivery device into a vessel, and manipulating the delivery device within the vessel so as to position the coil stent at a desired location therein. After placement, the coil stent is decoupled from the delivery device which is removed from the vessel, and the elastic memory is allowed to expand the coil stent into contact with the inner walls of the vessel and to a diameter substantially greater than the predetermined diameter. The use of an inherently expandable plastic coil stent permits the effective prevention of restenosis in small arteries typically found in the area of the heart.

According to certain features of the invention, the providing step comprises winding the filament on a mandrel, applying heat to the mandrel retained base coil so as to relieve substantially all strain therein, and removing the base coil from the mandrel; and the inducing step comprises subjecting the base coil to electron beam radiation so as to cause cross linkage of the molecules therein. The application of electron beam radiation both sterilizes the base coil and establishes a set thereof at the given diameter.

According to other features of the invention, the delivery device comprises an elongated cable, the coupling step comprises inserting the coil stent into a compartment portion of the delivery device, and the decoupling step comprises activating the cable to apply a force that ejects the coil stent from the compartment portion. These steps enhance the efficient placement of the coil stent within the artery.

According to another feature of the invention, the providing step comprises adding an x-ray opaque material to the plastic material. The addition of x-ray opaque material facilitates monitoring movement of the coil stent within the artery.

According to yet another feature of the invention, the providing step comprises adding an anti-coagulate substance to the plastic material. Slow release of the anti-coagulate material after placement of the coil stent helps to prevent blood clotting.

According to still another feature of the invention, the plastic material is a high density polyethylene having a specific gravity greater than 0.95. This material is uniquely suited for use in the method of the invention.

According to an important feature of the invention, the expansion of the coil stent to the diameter substantially greater than the predetermined diameter requires a time period greater than 15 seconds. The use of a plastic coil stent exhibiting a relatively slow rate of recovery from its predetermined diameter significantly reduces the procedural problems associated with its use.

According to other important features of the invention, the inserting, manipulating, and removing steps are performed in an operating room; and the forming step is performed in the operating room immediately prior thereto. This procedure facilitates implantation of the coil stent before any loss of its elastic memory.

According to still other important features of the invention, the providing step comprises winding the filament on a mandrel to form the base coil having the given diameter and a predetermined length, packaging the base coil in a sterile package, and removing the base coil from the package; and the forming step comprises cutting a given length portion from the base coil to provide the coil stent. These procedures insure the ready availability of coil stents of a selected length.

The invention further encompasses a coil stent composed of high density polyethylene having a specific density greater than 0.95, having a substantially uniform predetermined diameter and formed from a base coil having a substantially uniform given diameter substantially greater than the predetermined diameter and comprising molecules cross linked by electron beam radiation to provide an elastic memory that creates an inherent tendency for the coil stent to return to the given diameter. Such a coil stent is uniquely suited for use in the practice of the inventive method.

DESCRIPTION OF THE DRAWINGS

These and other objects and features of the invention will become more apparent upon a perusal of the following description taken in conjunction with the accompanying drawings wherein:

FIG. 1 is a cross sectional view illustrating a coil stent and delivery catheter of the present invention;

FIG. 2 is a cross sectional view of a mandrel wound base coil used to form the coil stent shown in FIG. 1; and FIG. 3 is a cross sectional view of the base coil of FIG. 2 disposed in a sterile package.

DESCRIPTION OF THE PREFERRED EMBODIMENT

The method of the present invention employs a plastic coil stent 11 that is implanted in a vessel (not shown) of a living body by a delivery device 12. Included in the delivery device 12 is an elongated hollow catheter 13 and an open ended tubular pouch 14 disposed at an end thereof. The catheter 13 is about 40 inches in length and comprises a hollow coiled push cable 15 covered by a jacket 16. Preferably, the push cable 15 is a mandrel wound, Teflon coated stainless steel wire coil freely flexible in any direction and having an outside diameter of about 0.034 inches and an inside diameter of about 0.017 inches. The outer jacket 16 preferably is an extruded Teflon sleeve having a minimum inside diameter of 0.036 inches and an outside diameter of about 0.050 inches. Because of the Teflon jacket 16 and the Teflon coating on the push cable 15, movement thereof within the jacket 16 is accomplished with a minimum of drag friction. The pouch 14 preferably is about 3.5 inches long, has an outside diameter of about 0.075 inches and an inside diameter of 0.064 inches.

The coil stent 11 utilized in the invention is formed from plastic, preferably a high density polyethylene of the Olephene family with a specific gravity greater than 0.95. Compounded with the polyethylene in an amount of about 3 to 6% by weight is a suitable x-ray opaque material such as bismuth-sub-carbonate. Also preferably compounded with the polyethylene is a very small percentage of an anti-coagulate substance.

After compounding, the polyethylene is extruded into a filament having a diameter of between 0.015 inches and 0.016 inches. The filament then is wound on a suitable steel wire mandrel 23 with a diameter of between 0.031 inches and 0.032 inches into a base coil 25 as shown in FIG. 2. Next, the base coil 25 still secured to the mandrel 23 is heated in an oven (not shown) at a temperature of about 250° F. for a sufficient time period to relieve all strains in the polyethylene filament. The mandrel 23 then is removed from the oven and allowed to cool to room temperature after which the base coil 25 is carefully removed. After removal, the resultant base coil 25 preferably has a length of approximately 6 inches, an inside diameter of approximately 0.375 inches and an outside diameter of approximately 0.405 inches. The base coil 25 then is subjected to electron beam radiation causing cross linkage of its molecules and thereby imparting an elastic memory to the polyethylene material. Consequently, if the diameter of base coil 25 is subsequently distorted and then released, the elastic memory created by the electron beam radiation will cause the coil 25 to return to its original given diameter. After formation in the manner described above, the base coil 25 is sterile packaged in a package 27 as shown in FIG. 3.

Prior to the practice of the present invention, conventional percutaneous transluminal balloon angioplasty is performed in the following manner. A small lead wire 21 (FIG. 1) is inserted into a selected artery of a particular patient and very slowly fed to a region in which a stenosis exists. The movement of the lead wire 21 is carefully observed on a floroscope screen. When the lead wire 21 is in a desired position, a balloon catheter (not shown) is fed over the lead wire which functions as a guide track. Once properly positioned, the catheter retained balloon is inflated to a specified pressure and maintained in an inflated state for a specified time. Subsequently, the balloon is deflated and together with the catheter is removed from the artery. However, the lead wire 21 is retained in position within the artery for use in placement of the stent 11 as described hereinafter.

Within an operating room used for the angioplasty procedure, a base coil 25, previously removed from its sterile package 27, is provided in a sterile machine (not shown). That machine winds the base coil 25 on a mandrel of predetermined diameter to provide the coil stent 11 having a temporary set at a predetermined diameter less than the original given diameter of the base coil 25. For coronary angioplasty procedures, the resultant coil preferably has an inside diameter of approximately 0.0315 inches and an outside diameter of approximately 0.0625 inches. The coil stent 11 then is cut by a medical attendant into a desired length determined by the size of the stenosis being treated. Next, the prepared stent 11 is coupled to the delivery catheter 13 by being deposited into the compartment provided by the pouch 14 and the catheter 16 is inserted into the treated artery vessel and guided therein by the previously positioned guide wire 21. Because of its x-ray opaque material content, movement of the stent 11 within the vessel can be monitored on a floroscope screen. Once the pouch 14 and retained stent 11 have reached the desired location in the vessel, the push cable 15 is moved within the jacket 16 to engage and eject the stent 11 out of the open end of the pouch 14. Ejection of the stent 11 is accomplished by pushing a knob 31 fixed to the push cable 15 so as to produce movement thereof relative to a knob 32 fixed to the jacket 16. All of the above procedures will typically be accomplished within a few minutes after formation of the coil stent 11 from the base coil 25. After ejection, its elastic memory will cause the coil stent 11 to slowly increase in diameter over a relatively long period of, for example, a minute or more until engaging the inner walls of the treated vessel. The delivery catheter 13 and the lead wire 21 then are removed while the stent 11 remains in position within the patient. Thereafter, the expanded stent 11 will maintain in the treated vessel the opening created by the angioplasty procedure.

Obviously, many modifications and variations of the present invention are possible in light of the above teachings. For example only, although the described method has preferred application to the prevention of arterial restenosis after angioplasty, the disclosed procedure and coil stent 11 also can be used to maintain long term patentcy of other ducts within a living body. It is to be understood, therefore, that the invention can be practiced otherwise than as specifically described.

What is claimed is:

1. A method for preventing arterial restenosis after angioplasty, comprising the steps of:

winding a plastic material filament into a helical base coil having a cross-section of substantially uniform given diameter; said providing step comprising the step of inducing in said filament an elastic memory that provides an inherent tendency for said base coil to return to said given diameter after any distortion thereof;

forming from said base coil a helical coil stent with a cross-section having a substantially uniform predetermined diameter substantially less than said given diameter;

releasably coupling said coil stent to an elongated delivery device adapted to pass through a blood carrying vessel;

inserting said coil stent and delivery device into a vessel;

manipulating said delivery device within the vessel so as to position said coil stent at a desired location therein;

decoupling said coil stent from said delivery device;

removing said delivery device from the vessel; and allowing said elastic memory to expand said coil stent into contact with the inner walls of the vessel and to a diameter substantially greater than said predetermined diameter.

2. A method according to claim 1 wherein said forming step comprises winding said base coil on a mandrel so as to produce said coil stent with a temporary set at said predetermined diameter.

3. A method according to claim 2 wherein said inducing step comprises subjecting said base coil to electron beam radiation so as to cause cross linkage of the molecules therein.

4. A method according to claim 3 wherein said providing step comprises winding said filament on a mandrel, applying heat to said mandrel retained base coil -so- as to relieve substantially all strain therein, and removing said base coil from the mandrel.

5. A method according to claim 4 wherein said coupling step comprises inserting said coil stent into a compartment portion of said delivery device, and said decoupling step comprises ejecting said coil stent from said compartment portion.

6. A method according to claim 5 wherein said providing step comprises adding an x-ray opaque material to said plastic material.

7. A method according to claim 5 wherein said providing step comprises adding an anti-coagulate substance to said plastic material.

8. A method according to claim 5 wherein said plastic material is a high density polyethylene having a specific gravity greater than 0.95.

9. A method according to claim 1 wherein said providing step comprises winding said filament on a mandrel to form said base coil having said given diameter and a predetermined length, packaging said base coil in a sterile package, and removing said base coil from said package; and said forming step comprises winding a portion of said base coil on a mandrel so as to provide therefore said predetermined diameter, and detaching said portion from said base coil to provide said coil stent.

10. A method according to claim 9 wherein said inducing step comprises subjecting said base coil to electron beam radiation so as to cause cross linkage of the molecules therein.

11. A method according to claim 10 wherein said providing step comprises winding said filament on a mandrel, applying heat to said mandrel retained base coil so as to relieve substantially all strain therein, and removing said base coil from the mandrel.

12. A method according to claim 1 wherein said expansion of said coil stent to said diameter substantially greater than said predetermined diameter requires a time period greater than 15 seconds.

13. A method according to claim 12 wherein said forming step comprises winding said base coil on a mandrel so as to produce said coil stent with a temporary set at said predetermined diameter.

14. A method according to claim 13 wherein said inducing step comprises subjecting said base coil to electron beam radiation so as to cause cross linkage of the molecules therein.

15. A method according to claim 14 wherein said providing step comprises winding said filament on a mandrel, applying heat to said mandrel retained base coil so as to relieve substantially all strain therein, and removing said coil stent from the mandrel.

16. A method according to claim 12 wherein said providing step comprises winding said filament on a mandrel, applying heat to said mandrel retained base coil so as to relieve substantially all strain therein, and removing said coil stent from the mandrel.

17. A method according to claim 1 wherein said inducing step comprises subjecting said base coil to electron beam radiation so as to cause cross linkage of the molecules therein.

18. A method according to claim 1 wherein said providing step comprises winding said filament on a mandrel, applying heat to said mandrel retained base coil so as to relieve substantially all strain therein, and removing said base coil from the mandrel.

19. A method according to claim 1 wherein said inserting, manipulating, and removing steps are performed in an operating room; and said forming step is performed in the operating room prior thereto.

20. A method according to claim 19 wherein said providing step comprises winding said filament on a mandrel to form said base coil having said given diameter and a predetermined length, packaging said base coil in a sterile package, and removing said base coil from said package; and said forming step comprises winding a portion or said base coil on a mandrel so as to provide therefore said predetermined diameter, and detaching said portion from said base coil to provide said coil stent.

21. A method according to claim 5 wherein said delivery device comprises an elongated cable and said decoupling step comprises the step of activating said cable to apply a force that ejects said coil stent from said compartment portion.

* * * * *